(12) United States Patent
Bardat et al.

(10) Patent No.: US 9,358,275 B2
(45) Date of Patent: *Jun. 7, 2016

(54) FACTOR VII COMPOSITION

(71) Applicant: Laboratoire Francais Du Fractionnement Et Des Biotechnologies, Les Ulis (FR)

(72) Inventors: Annie Bardat, Limours (FR); Cornelius Pompe, Munich (DE)

(73) Assignee: Laboratorie Francais du Fractionnement et des Biotechnologies, Les Ulis (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/687,499

(22) Filed: Apr. 15, 2015

(65) Prior Publication Data

US 2015/0216951 A1    Aug. 6, 2015

Related U.S. Application Data

(63) Continuation of application No. 13/377,680, filed as application No. PCT/FR2010/051229 on Jun. 18, 2010, now Pat. No. 9,029,316.

(30) Foreign Application Priority Data

Jun. 26, 2009   (FR) ...................... 09 54390

(51) Int. Cl.
*A61K 38/48* (2006.01)
*A61P 7/04* (2006.01)
*C12N 9/64* (2006.01)
*A61K 47/18* (2006.01)
*A61K 9/00* (2006.01)
*A61K 47/12* (2006.01)

(52) U.S. Cl.
CPC ........... *A61K 38/4846* (2013.01); *A61K 9/0019* (2013.01); *A61K 47/12* (2013.01); *A61K 47/183* (2013.01); *C12N 9/6437* (2013.01); *C12Y 304/21021* (2013.01)

(58) Field of Classification Search
None
See application file for complete search history.

(56) References Cited

U.S. PATENT DOCUMENTS

2006/0247426 A1    11/2006    Bardat et al.

FOREIGN PATENT DOCUMENTS

| WO | WO 01/12653 | 2/2001 |
| WO | WO 2005/016365 | 2/2005 |
| WO | WO 2006/089954 | 8/2006 |
| WO | WO 2007/022784 | 3/2007 |
| WO | WO-2008/078189 A2 | 7/2008 |
| WO | WO 2008/113589 | 9/2008 |
| WO | WO-2008/135500 A1 | 11/2008 |

*Primary Examiner* — Julie Ha
*Assistant Examiner* — Kristina M Hellman
(74) *Attorney, Agent, or Firm* — Cesari and McKenna LLP

(57) ABSTRACT

A stable pharmaceutical composition in liquid form or in solid form, containing factor VII. The composition is free of mannitol, sucrose, and any antioxidant.

19 Claims, 1 Drawing Sheet

FACTOR VII COMPOSITION

CROSS-REFERENCE TO RELATED APPLICATIONS

The present application is a continuation of commonly assigned U.S. patent application Ser. No. 13/377,680 filed on Dec. 12, 2011, now U.S. Pat. No. 9,029,316; which is the National Stage of International Application PCT/FR2010/051229 filed on Jun. 18, 2010; which claims the benefit of French Patent Application 0954390 filed on Jun. 26, 2009. The contents of these applications are hereby incorporated by reference in their entirety.

BACKGROUND OF THE INVENTION

1. Field of the Invention

The present invention relates to a stable pharmaceutical composition comprising factor VII (FVII).

2. Background Information

The coagulation phenomenon comprises a cascade of enzymatic reactions involving coagulation factors of which several are proteases comprising a serine in their active site. The final step is the conversion of soluble fibrinogen into fibrin filaments which surround circulating cells in their meshes. Coagulation factors are denoted by numbers ranging from I to XIII. With the exception of factor XIII, which is involved in the final step of coagulation, the other factors are involved in reverse order of their numbering; thus, factor XII initiates coagulation and factor I ends it. Each factor exists in the form of an inactive precursor and in activated form, indicated by the letter a.

Coagulation involves two pathways, one intrinsic, the other extrinsic, resulting in a common final pathway. The combination of the two mechanisms ensures the formation of a solid and flexible blood clot, which withstands blood pressure while at the same time guaranteeing sufficient mobility. Under the action of thrombin, fibrinogen undergoes chemical modifications which result in the formation of fibrin. Fibrin is necessary for clot formation.

The intrinsic pathway comprises the factors present in the circulation and the coagulation process begins right within the blood vessel. The extrinsic pathway, for its part, involves tissue factors that are not normally present in the circulation and that are released during vascular damage. It is when this pathway is activated that a chain reaction occurs, during which an activated coagulation factor triggers the activation of the subsequent coagulation factor. This pathway involves the intervention of factor VII (FVII) present in the plasma. Activated factor VII, also called proconvertin, is one of the factors, having a molecular weight of approximately 50 kDa, involved in the blood coagulation mechanism. It is a glycoprotein of the serine protease family, the synthesis of which in activated form is vitamin K-dependent. In order to initiate the coagulation cascade, FVII must be activated to FVIIa. FVIIa alone (not complexed) has a weak proteolytic activity. Then, once activated, FVIIa complexes with tissue factor (TF), a phospholipid-associated protein, which is released during the vascular damage. The FVIIa-TF complex subsequently converts factor X to factor Xa in the presence of calcium ions. This complex also acts on the activation of FIX to FIXa, thus catalysing the intrinsic pathway. Factors IXa and Xa in return activate the activated factor VII. Factor Xa complexed with activated factor FV and with prothrombinase, converts prothrombin to thrombin. Thrombin then acts on fibrinogen in order to convert it to fibrin and also allows the activation of FVIIIa and of FVa from, respectively, FVIII and FV. Thrombin makes it possible, for its part, when it is in the presence of calcium, to activate factor XIIIa responsible for consolidation of the fibrin clot.

Nevertheless, when a coagulation factor is lacking, the cascade of reactions is interrupted or defective and the term abnormal coagulation is then applied.

Activated factor VII acts locally in the presence of tissue factor released after tissue damage causing haemorrhage, even in the absence of factor VIII or IX. For this reason, factor VII, preferably in activated form, has been used for a long time for the treatment of certain blood coagulation disorders manifested by bleeding. The factor is involved in many pathological conditions, such as haemophilia type A or B, in which the patients exhibit factor VIII or IX inhibitors, acquired haemophilia or congenital factor VII deficiency, and as a product for preventing haemorrhages that can occur during surgical operations.

At the current time, a medicament available on the market for the treatment of these patients suffering from haemophilia or from congenital factor VII deficiency is known. It is NovoSeven®, authorized on the European market since 1996 and authorized on the American market in 1999, produced by the Danish company NovoNordisk. NovoSeven® is a medicament of which the active ingredient is eptacog alfa (recombinant human activated coagulation factor VII produced by genetic engineering from BHK baby hamster kidney cells). This product also contains sodium chloride (2.92 g/l), calcium chloride dihydrate (1.47 g/l), glycylglycine (1.32 g/l), polysorbate 80 (0.07 g/l) and mannitol (30 g/l).

A variant of NovoSeven also exists, called NovoSeven® RT, which enables storage of the product at room temperature (25° C.). This second product consists of sodium chloride (2.92 g/l), calcium chloride dihydrate (1.47 g/l), glycylglycine (1.32 g/l), polysorbate 80 (0.07 g/l), mannitol (25 g/l), and hydrochloric acid and sodium hydroxide for adjusting the pH, and also contains sucrose (10 g/l) and methionine (0.5 g/l) (used as antioxidant). The returning of this product to solution requires water for injection, but also histidine. NovoSeven® RT was authorized on the European and American markets in 2008.

The main therapeutic indication for recombinant FVIIa (rFVIIa) concerns the treatment of spontaneous or surgical bleeding in type A haemophiliacs having developed anti-factor VIII antibodies and type B haemophiliacs having developed anti-factor IX antibodies. In Europe, it is also indicated for use in patients with a congenital FVII deficiency and in patients suffering from Glanzmann's thrombasthenia. In addition, numerous publications report the efficiency of rFVIIa in controlling haemorrhage during surgical procedures, in patients who have neither a congenital deficiency in a coagulation factor nor thrombasthenia.

An article by Nedergaard et al., 2008 [Nedergaard H. et al., In vitro stability of lyophilized and reconstituted recombinant activated factor VII formulated for storage at room temperature, Clinical Therapeutics, Vol 30, No. 7, p 1309-1315, 2008] teaches that NovoSeven® RT remains stable for a period of 24 months at 25° C., 12 months at 30° C., 6 months at 40° C. and 12 hours at 50° C. and 60° C. in its lyophilized form. Furthermore, this product is stable only for six hours after liquid reconstitution thereof, and consequently it is recommended to perform the injection within three hours following reconstitution. This product therefore exhibits, by virtue of this stability, handling difficulties and constraints in terms of administration times.

Patent EP 1 210 361 discloses the advantage of using glycylglycine for stabilizing a lyophilized composition of activated factor VII.

Patent application WO 2004/000347 proposes various other stabilizing agents.

The publication by Soenderkaer S. et al., 2004 [Soenderkaer S. et al., Effects of sucrose on rFVIIa aggregation and methionine oxidation, European Journal of Pharmaceutical Sciences, Vol 21, p 597-606, 2004] describes sucrose as an essential excipient for stabilization against aggregation and heat denaturation of activated factor VII. According to this teaching, sucrose enables the protein to retain its native form in aqueous solution, by excluding sugars from the surface of the proteins, which makes it possible to increase the chemical potential of the molecule. Consequently, and by reducing its surface area, the protein remains in a compact conformation. The presence of sucrose as an excipient makes it possible to stabilize the activated factor VII in its lyophilized form.

However, the presence of sucrose leads to the induction of antioxidant compounds in the formulation, resulting in technical and regulatory constraints associated with the addition of compounds of this type.

There is therefore today a real need to develop medicaments containing factor VII which are free of antioxidants, chemically and physically stable at room temperature, and easy for patients to use, in particular patients suffering from haemophilia or from congenital factor VII deficiency.

SUMMARY OF THE INVENTION

The invention provides a pharmaceutical composition in liquid form or in solid form, comprising factor VII, preferably in the form of factor VIIa, said composition being free of mannitol and of sucrose.

According to one preferred embodiment, the composition is also free of any antioxidant.

Preferably, the composition comprises at least one hydrophilic amino acid or amino acid bearing a positively charged side chain, such as arginine.

According to one preferred embodiment, the composition of the invention comprises factor VII, at least one hydrophilic amino acid or amino acid bearing a positively charged side chain, at least one hydrophobic amino acid, and an alkali metal salt, an alkaline-earth metal salt, or a salt of a transition metal, said composition being free of mannitol and of sucrose.

Advantageously, the composition in solid form can be in the form of a powder or a cake (or plug). The composition preferably has a degree of moisture of less than or equal to 3%. According to one particular embodiment, the composition is in lyophilized form.

Another subject of the invention is a method for preparing such a composition, said method comprising mixing FVII with a buffer solution, adjusting the pH if necessary, and filtering so as to obtain a liquid form. This liquid form can subsequently undergo desiccation in order to obtain the solid form.

The term "buffer solution" includes at least one hydrophilic amino acid or amino acid bearing a positively charged side chain, and an alkali metal salt, an alkaline-earth metal salt, or a transition metal salt.

Advantageously, the buffer solution also contains at least one hydrophobic amino acid.

Another subject of the invention consists of a method for preparing an injectable formulation for therapeutic use, said method comprising dissolving a solid composition as defined herein, in water for injection.

The invention is also directed towards an injectable formulation that can be obtained by means of this method.

BRIEF DESCRIPTION OF THE DRAWINGS

The invention description below refers to the accompanying drawings, of which.

DETAILED DESCRIPTION

Figure 1:
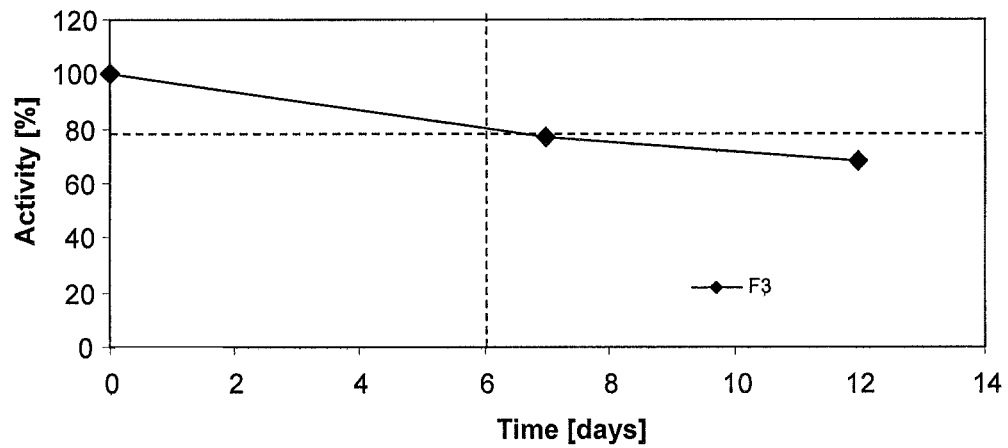
FIG. 1 is a graph which shows that the activity of FVIIa resulting from the formulation F3 is preserved after it has been reconstituted in liquid form, following storage for 6 days at 25° C.

The applicant provides factor VII compositions which are chemically and physically stable at room temperature and easy for patients suffering in particular from haemophilia or from congenital factor VII deficiency to use.

In particular, the novel pharmaceutical composition of the invention has a stability in solid form of greater than 24 months at a temperature less than or equal to 25° C.

The composition can therefore be stored at room temperature without substantial degradation of the factor VII. The term "room temperature" is intended to mean the temperature inside a room, normally included between 10° C. and 30° C., preferably between 15° C. and 25° C.

The term "factor VII" or "FVII" includes polypeptides comprising the sequence 1-406 of wild-type human factor VII (as described in U.S. Pat. No. 4,784,950), or of FVII derived from another species (for example, bovine, porcine, canine, murine). It also comprises the natural allelic variations of factor VII that can exist, and any form or degree of glycosylation or other post-translational modification.

The term "factor VII" also includes the FVII variants which have the same or a greater biological activity compared with the activity of the wild-type form, these variants including in particular the polypeptides differing from wild-type FVIIa by insertion, deletion or substitution of one or more amino acids.

"Factor VII" or "FVII" comprises uncleaved FVII (zymogen) and activated factor VII. Factor VII is used in the composition preferably in its activated form.

The term "biological activity of factor VIIa" includes the ability to generate thrombin, for example at the surface of activated platelets. The activity of factor VII in the composition can be evaluated in various ways. For example, it can be measured by the ratio between the amount of factor VIIa determined using a coagulation test and the amount of factor VII determined by immunoreactivity with anti-FVII antibodies.

The term "stable composition" signifies herein that the formation of aggregates (insoluble or soluble) is minimized, and/or that the chemical degradation is reduced, the pH is maintained and the conformation of the protein is not substantially modified during the production or the storage of the compositions of the invention, such that the biological activity and the stability of the protein are retained. When the compositions are subjected to lyophilization, the stabilization of the compositions involves lyoprotection and cryoprotection of the protein.

The term "physical stability" of factor VII refers to the reduction or absence of formation of insoluble or soluble aggregates of the dimeric, oligomeric or polymeric forms of factor VII, and also to the reduction or absence of any structural denaturation of the molecule.

The term "chemical stability" refers to the reduction or absence of any chemical modification of the factor VII during storage, in the solid state or in dissolved form, under accelerated conditions. For example, hydrolysis, deamination and/or oxidation phenomena are prevented or delayed. The oxidation of sulphur-containing amino acids is limited.

For example, the solid compositions of the invention contain low contents of oxidized forms and of aggregates at the end of the preparation method and before storage, for example less than 5% by weight, preferably less than 4%, or else less than 3% or less than 2% by weight of FVII is converted to the oxidized form, and less than 5% by weight, preferably less than 4%, or else less than 3% or less than 2% by weight of FVII is converted to the dimeric or polymeric form. During storage, preferably less than 10% by weight of FVII is converted to the oxidized form, and less than 10% by weight of FVII is converted to the dimeric or polymeric form, after storage at 30° C. after 24 months in the dark.

A lyophilized composition according to the invention also exhibits a structural stability, i.e. it is capable of forming a cake (or plug) which does not spontaneously crumble, and which is readily soluble in water before use.

The pharmaceutical composition of the invention is a composition in liquid form or in solid form, comprising factor VII, said composition being free of mannitol and of sucrose.

The content of factor VII, preferably in the form of factor VIIa, in the composition of the invention may be the following: between 0.1 and 15 mg/ml, preferably between 0.1 and 10 mg/ml, more preferably between 0.2 and 5 mg/ml, or else between 0.2 and 2 mg/ml (measured in liquid form, preferably before desiccation, or optionally after reconstitution in the form of an injectable preparation).

Preferably, the composition is free of any sugar, of polyol or of methionine.

The sugars to be avoided include, in particular, in addition to sucrose, di- and trisaccharides and polysaccharides, such as dextrose, lactose, maltose, trehalose, cyclodextrins, maltodextrins and dextrans.

The polyols to be avoided include, in particular, in addition to mannitol, sorbitol and xylitol.

More preferably, the composition is free of glycylglycine.

According to one preferred embodiment, the composition of the invention is also free of any antioxidant. The antioxidants include, for example, one or more of the following compounds: homocysteine, cysteine, cystathionine, methionine, glutathione.

The composition according to the invention comprises at least one hydrophilic amino acid or amino acid bearing a positively charged side chain, and optionally also at least one hydrophobic amino acid. The hydrophilic (or polar) amino acids or the amino acids bearing a positively charged side chain include lysine, arginine, histidine, glycine, serine, threonine, tyrosine, asparagine and glutamine.

Among the hydrophilic amino acids or amino acids bearing a positively charged side chain, use may preferentially be made of arginine, or one of its derived salts such as arginine hydrochloride or else arginine phosphate.

Amino acids such as glycine and/or lysine, or one of its derived salts such as lysine hydrochloride, can be advantageously added.

The addition of a hydrophilic amino acid or amino acid bearing a positively charged side chain, such as arginine, and where appropriate of a hydrophobic amino acid, or even of an alkali metal, alkaline-earth metal or transition metal salt, promotes the stabilization of factor VII and the solubilization of the lyophilized forms.

The hydrophobic amino acids (comprising an apolar side chain) include in particular the following amino acids: alanine, valine, leucine, isoleucine, phenylalanine, tryptophan and proline.

Preferably, the hydrophobic amino acid in the context of this invention is isoleucine, leucine or a mixture of both.

Preferentially, the composition of the invention comprises an alkali metal salt, an alkaline-earth metal salt, or a transition metal salt. Mention may in particular be made of trisodium citrate, calcium chloride or zinc chloride. Preferably, the salt used is preferentially sodium citrate or calcium chloride.

Finally, the composition of the invention may comprise one or more detergents of non-ionic type, such as polysorbates, poloxamers, polyoxyethylene alkyl ethers, a block copolymer of ethylene/polypropylene and polyethylene glycol. Advantageously, the preferred detergents are polysorbate 80 and polysorbate 20.

In one implementation example, the composition comprises:
factor VII, preferably in the form of factor VIIa;
arginine, optionally in hydrochloride form;
isoleucine;
lysine;
glycine;
trisodium citrate or calcium chloride;
and, where appropriate, polysorbate 80 or polysorbate 20.
More particularly, the composition may comprise
factor VII, preferably in the form of factor VIIa;
from 10 to 40 g/l of arginine, optionally in hydrochloride form;
from 4.2 to 6.6 g/l of isoleucine;
from 0.6 to 1.8 g/l of lysine;
from 0.6 to 1.8 g/l of glycine;
from 1 to 2 g/l of trisodium citrate dihydrate or from 0 to 0.2 g/L of calcium chloride dihydrate;
and, where appropriate, from 0 to 0.5 g/l of polysorbate 80.
According to one particular example, the composition comprises
factor VII (preferably in the form of factor VIIa) at 0.2 to 2 g/l,
arginine hydrochloride at 24 g/l,
isoleucine at 6 g/l,
trisodium citrate dihydrate at 1.5 g/l,
glycine at 1.2 g/l,
lysine hydrochloride at 1.2 g/l,
and/or polysorbate 80 at 0.07 g/l.
According to another particular example, the composition comprises
factor VII (preferably in the form of factor VIIa) at 0.2 to 2 g/l,
arginine hydrochloride at 34 g/l,
calcium chloride dihydrate at 0.15 g/l,
isoleucine at 6 g/l.
The concentrations are determined with respect to the compositions in liquid form, before desiccation, or after reconstitution in the form of an injectable preparation.

The Applicant has removed sucrose and also mannitol from its composition for pharmaceutical use, these ingredients nevertheless normally being used as diluents or stabilizers of pharmaceutical formulations comprising factor VII.

The absence of sucrose and of mannitol offers several advantages. Firstly, the presence of oxidizing components or of endotoxins, which can be introduced via the sucrose, is avoided.

It surprisingly emerged that the absence of mannitol allows to prevent the formation of polymorphic forms of mannitol crystals within the composition during lyophilization, and limits the risk of impurities, such as in particular the presence of mannose in the composition.

Moreover, against all expectations, the absence of mannitol and of sucrose from the composition of the invention is not detrimental to the stability of the composition. On the contrary, an increase in the glass transition temperature of the composition, relative to the available formulations, for example NovoSeven® RT, is observed.

Glass transition is a second-order transition, i.e. a thermal transition which involves a change in heat capacity, but no latent heat.

It is characteristic of supercooled liquids which are cooled to a sufficiently low temperature sufficiently quickly, without crystallizing, and which become a glass, and of amorphous polymers or of the amorphous part of crystalline polymers which go from a solid state to a viscoelastic state. The glass transition temperature or Tg is the temperature at which this change of state takes place. When a liquid product is cooled below this temperature, it becomes solid and brittle, like glass, and is said to be in the glassy state.

Since the mobility of the molecules is blocked when the product is in the glassy state (only the free-radical functional groups still have a low relative mobility), it is advantageous to store the products at temperatures below their glass transition. A high glass transition temperature therefore promotes better stability of the lyophilized composition at high temperatures (>25° C.) and thus decreases the reactivity of the active ingredient [Pikal et al., The Effects of Formulation Variables on the Stability of Freeze-Dried Human Growth Hormone, Journal of Pharmaceutical Research, Vol 8, p 427-436, 1991].

Furthermore, by virtue of its formulation, the composition for pharmaceutical use according to the invention prevents aggregation of the protein.

Indeed, in the presence of mannitol and of sucrose as in the NovoSeven® RT formulation, the glass transition temperature is 45° C. The glass transition temperature of the composition of the invention, which is free of sucrose and of mannitol, is above 60° C., and generally between 74 and 93° C., which makes it possible to envisage storage outside a refrigerator and even at temperatures above 25° C. (cf. FIG. 2).

The factor VII is generally a human factor VII. It can be obtained in various ways, for example from the non-cryoprecipitable fraction of human plasma, or by genetic engineering from cells, or else from transgenic animals.

Preferably, the factor VII (preferably in the form of factor VIIa) is produced in particular in the milk of a transgenic animal, the formulation of the invention making it possible for the factor VII to retain a satisfactory biological activity after lyophilization.

In one preferred embodiment, the human factor VII is produced in the milk of nonhuman transgenic mammals genetically modified so as to produce this protein. Preferably, it is the milk of a transgenic doe rabbit or of a transgenic goat.

The secretion of factor VII by the mammary glands, which enables its secretion in the milk of the transgenic mammal, involves controlling the expression of the factor VII in a tissue-dependent manner. Such methods of control are well known to those skilled in the art. The expression is controlled by virtue of sequences which allow the expression of the protein towards a particular tissue of the animal. They are in particular WAP, beta-casein and beta-lactoglobulin promoter sequences and signal peptide sequences. The method for extracting proteins of interest from the milk of transgenic animals is described in patent EP 0 264 166.

The composition of the invention can be obtained using any customary technique.

In particular, the composition of the invention can be obtained by carrying out a method comprising mixing the factor VII with a buffer solution, adjusting the pH if necessary, filtering so as to obtain a liquid form, and then desiccating, if necessary, so as to obtain a solid form.

Preferably, the pH of the solution before desiccation is between 4.0 and 9.0, more particularly in the ranges between 4.0 and 8.0; 4.0 and 7.5; 4.5 and 7.5; 5.0 and 7.5; 5.5 and 7.0; 6.0 and 7.5; 6.5 and 7.5.

Desiccation is a process for extensive elimination of water. It is a dehydration aimed at eliminating as much water as possible. This phenomenon may be natural or forced. This desiccation can be carried out by means of lyophilization, spray-drying or cryo-spray-drying techniques. The preferred method for obtaining the solid form of the composition for pharmaceutical use according to the invention is lyophilization.

Lyophilization methods are well known to those skilled in the art, see, for example [Wang et al., Lyophilization and development of solid protein pharmaceuticals, International Journal of Pharmaceutics, Vol 203, p 1-60, 2000].

Other methods suitable for reducing the degree of moisture or the water content of the composition can be envisaged. Preferably, the degree of moisture is less than or equal to 3% by weight, preferably less than or equal to 2.5%, preferably less than or equal to 2%, preferably less than or equal to 1.5%.

The composition according to the invention may be advantageously subjected to a method for elimination or inactivation of infectious agents, for example by dry-heating the lyophilisate.

The solid composition according to the invention, preferably in lyophilized form, can be dissolved in water for injection (WFI), so as to obtain a formulation for therapeutic use.

Preferably, the factor VII can be dissolved in pure water, which is advantageous compared with more complex reconstitution solvents, such as the solvent with histidine used in the NovoSeven® RT product.

The liquid composition (before desiccation) according to the invention has a chemical or physical stability of at least 3 days between 2 and 8° C.

The solid composition according to the invention has a chemical or physical stability in solid form of greater than 24 months, and generally up to at least 36 months, at a temperature less than or equal to 25° C. The reconstituted injectable formulation is also very stable, its chemical and physical stability in liquid form being greater than 6 hours at 25° C., preferably greater than 12 hours, preferably greater than 24 h, more preferably greater than one week.

The pharmaceutical composition in liquid form or solid form or the injectable formulation is of use for the treatment of various pathological conditions.

A subject of the invention is a pharmaceutical composition, or injectable formulation as defined above, for use in the treatment of haemophilia or of congenital factor VII deficiency.

A method for treating haemophilia or congenital factor VII deficiency, in which an effective amount of the injectable formulation described is administered to a patient requiring such a treatment, is also described.

The haemophilia may be type A or type B. Haemophilia type A is characterized by a factor VIII deficiency, whereas haemophilia type B, for its part, is the result of a factor IX deficiency. Congenital factor VII deficiency is a rare hereditary haemorrhagic disease inherited by autosomal recessive transmission, caused by a decrease in or an absence of coagulation factor VII.

The injectable formulation can be administered parenterally (intravenously, subcutaneously, intramuscularly), in an amount assessed by the practitioner. The administration of the liquid form (before desiccation) or of the solid form, via any suitable route and any suitable means, is not excluded.

The following examples and figures illustrate the invention without, however, limiting the scope thereof.

EXAMPLES

The FVII used in the examples is obtained from the milk of transgenic doe rabbits, as described in patent application WO 2008099077. It is human factor VII which is activated during its purification.

Example 1

Preparation of the Formulations 1.1: Preparation of Liquid Formulations F1 to F7:

Purified and activated factor VII (10-20 ml) at an approximate concentration of 0.6 mg/ml (formulations F1 to F5) and 0.4 mg/ml (formulations F6 and F7), respectively, was dialysed for 12 hours against 2 liters of buffer solution, as defined in the corresponding row in Table 1. The pH (6.0±0.2) was adjusted with either 1M NaOH or 1M HCl. The formulated FVIIa solutions were filtered and distributed into bottles in a proportion of 0.5 ml per bottle. The bottles were then pre-stoppered using bromobutyl stoppers.

1.2: Preparation of Lyophilized Formulations Resulting from the Liquid Formulations F1 to F7 Prepared in Point 1.1 Above:

The bottles were lyophilized according to a predefined cycle. In order to make it possible to detect the end of the desiccation, the lyophilizer was equipped with a capacitance moisture sensor. At the end of the lyophilization cycle, the bottles were stoppered under vacuum and sealed with aluminium capsules.

1.3: Preparation of the Liquid Formulation F8:

Purified and activated factor VII (0.4 mg/ml) was formulated by buffer exchange on a Superdex 200 gel filtration column. The column was initially equilibrated with a buffer solution comprising trisodium citrate (1.0 g/l), arginine hydrochloride (30 g/l) and isoleucine (6.0 g/l) (see Table: F8). The pH (7.0±0.2) was adjusted. The concentration of the eluate was determined at approximately 0.4 mg/ml.

The formulated FVIIa solution was filtered and distributed into bottles in a proportion of 0.5 ml per bottle. The bottles were then pre-stoppered using bromobutyl stoppers.

1.4: Preparation of a Lyophilized Formulation Resulting from Liquid Formulation F8 Prepared in Point 1.3 Above:

The bottles were lyophilized according to a predefined cycle. In order to monitor the end of the desiccation, the lyophilizer was equipped with a capacitance moisture sensor. At the end of the lyophilization cycle, the bottles were stoppered under vacuum and sealed with aluminium capsules.

1.5: Preparation of the Liquid Formulation F9 and Lyophilization:

Purified and activated factor VII (approximately 0.4 mg/ml) was formulated by buffer exchange on a Superdex 200 gel filtration column. The column was initially equilibrated with a buffer solution comprising trisodium citrate (1.0 g/l), arginine hydrochloride (30 g/l) and isoleucine (6.0 g/l) (see Table: F9). The pH (7.0±0.2) was adjusted. Glycine (1.2 mg/ml) and lysine hydrochloride (1.2 mg/ml) were added.

The formulated FVIIa solution was filtered and distributed into bottles in a proportion of 1.0 ml per bottle. The bottles were then pre-stoppered using bromobutyl stoppers.

The bottles were then lyophilized in the same way as previously, and stored at 40° C. for 6 months.

1.6: Preparation of the Liquid Formulations F10 and F11 and Lyophilization:

Purified and activated factor VII at an approximate concentration of 1.0 mg/ml (F10) and 0.8 mg/ml (F11), respectively, was formulated by dialysis in tubing with the buffer as defined in tables 3 and 4 (see table: F10 and F11). The pH (7.0±0.2) was adjusted.

The formulated FVIIa solutions were filtered and distributed into bottles in a proportion of 1.0 ml per bottle. The bottles were then pre-stoppered using bromobutyl stoppers.

The bottles were then lyophilized in the same way as previously.

The formulation F10 was stored under the following conditions:
  liquid at 5° C. for 144 hours then at 25° C. for 6 hours,
  freezing and thawing cycle (4 consecutive cycles),
  lyophilized and stored at 25° C. and 40° C. for 6 months,
  frozen at <−70° C. for 6 months.

The formulation F11 was stored under the following conditions:
  liquid for 72 hours at 5° C. plus a further 6 hours at 25° C.,
  lyophilized and stored at 25° C. and 40° C.,
  frozen at <−70° C. in the buffer before the dialysis step:
  Trometamol (2.42 mg/ml), NaCl (8.77 mg/ml) and mannitol (30 mg/ml).

Example 2

Formulation Tests

Materials and Methods:

2.1. Measurements of Dynamic Light Scattering, Hereinafter "DLS"

500 microliters of each sample resulting from the lyophilization were placed in a microcuvette (Plastibrand®, Wertheim, Germany), which was transferred into a Zetasizer Nano instrument (Malvern Instruments, Worcestershire, UK). This instrument operates with a 4 mW He—Ne laser at 633 nm, and a non-invasive backscatter, or NIBS, technique.

The size distribution of the monomeric populations of the protein by intensity and volume was calculated using the Dispersion Technology Software from Malvern (version 4.00). The refractive indices of the material and of the dispersant were defined at 1.33 and 1.45, respectively. The temperature during the measurements was controlled and fixed at 20° C. Quality parameters for the formulations tested include the diameter of the population of proteins in monomer form and the intensity of scattering of the population of proteins.

2.2. Visual Inspection of the Formulations Reconstituted

The test formulation was reconstituted from the lyophilized formulation with 0.5 g of water for injection. The solvent was injected into the bottle of lyophilisate using a syringe, via the stopper.

After complete dissolution of the cake, the reconstituted product was examined according to the visual inspection method relating to the European Pharmacopoeia (Methods of Analysis—Pharmaceutical Technical Procedures—Particulate contamination-visible particles—paragraph 2.9.20).

The formulations tested were classified semi-quantitatively, according to their degree of contamination with visible particles:
- −=no visible particle
- ϵ=some rare visible particles
- +=small amount of visible particles
- ++=large amount of visible particles
- +++=very large amount of visible particles All the tests were carried out independently, and by three different operators.

2.3. Filter Test for Aggregate Detection

The method used is taken from the article [Li et al., A simple method for the detection of insoluble aggregates in protein formulations, Journal of Pharmaceutical Sciences Vol 96 (7), p 1840-1843, 2007].

A Millex® GV 0.2 μm sterile membrane filter was rinsed with 3 ml of water and then the same volume of buffer solution. 0.5 ml of protein (FVIIa) solution to be analysed was subsequently filtered through this filter. The filter was then rinsed again with equal volumes of water for injection (3 ml) and then of buffer solution (3 ml). The protein fractions retained by the filter were stained by adding 2 ml of staining solution (Reversible Protein Detection KIT from SIGMA). The staining solution was kept in contact with the filtration membrane for 5 min before flow. The membrane was then rinsed again as described above. The formulations tested were classified semi-quantitatively, according to their degree of stained particles observed on the filter, originating from proteins:
- −=No visible particle detected, originating from proteins
- ϵ=Some rare visible particles detected, originating from proteins
- +=Small amount of visible particles detected, originating from proteins
- ++=Large amount of visible particles detected, originating from proteins
- +++=Very large amount of visible particles detected, originating from proteins.

2.4. Determination of the Glass Transition Temperature (Tg)

The glass transition temperature was determined by means of a DSC 7 differential scanning thermoanalyser (Perkin Elmer) calibrated using indium (melting temperature (Tm) 156.6° C.) and n-octadecane (Tm 38.2° C.). The samples were subjected to temperatures from −50 to 138° C. at a speed of 20° C./min. Helium was used to carry out the experiments at a temperature below room temperature. The glass transition temperature was taken at the median point of the endothermic change in the apparent specific heat. Two measurements were carried out and the mean gives the Tg.

2.5. Determination of the FVIIa/FVII:Ag Ratio

The activity of the factor VII in the composition is evaluated by the ratio between the amount of factor VIIa determined using a coagulation test and the amount of factor VII determined by immunoreactivity with anti-FVII antibodies.

Assaying of factor VII (hereinafter denoted "factor VII antigen" or "FVIIAg"):

The FVII is assayed using an immunoenzymatic method (ELISA) with commercial reagents (Diagnostica Stago). Briefly, the factor VII to be assayed is captured by an anti-human factor VII antibody immobilized on a solid phase. The factor VII attached is then recognized by a peroxidase-conjugated immunoconjugate. The amount of peroxidase bound is measured through its activity on the substrate ortho-phenylenediamine in the presence of aqueous hydrogen peroxide. The intensity of the coloration, after the reaction has been stopped using a strong acid, depends on the amount of factor VII initially present in the sample.

Assaying of factor FVII in activated form:

The activated factor FVII (FVIIa) is measured using a chronometric method with commercial reagents (Diagnostica Stago). Recombinant soluble tissue factor (rsTF) has a factor VIIa cofactor function and allows plasma coagulation in the presence of phospholipids and calcium. In this system, the coagulation time obtained will be dependent on the amount of factor VII contained in the test sample. The rsTF does not activate factor VII to factor VIIa; consequently, the factor VII contained in the plasma does not interfere in the assay.

2.6: Molecular Size Distribution (MSD):

The molecular size distribution is determined by means of a chromatography system equipped with a pump, a thermostatic injector, a UV detector, and a computer acquisition system, using a Superdex Tricorn 200 10/300 GL column (GE Healthcare, ref. 17-5175-01). The mobile phase is composed of 0.01M phosphate buffer, 0.138M sodium chloride and 0.0027M potassium chloride at pH 7.4. Its flow rate is 0.4 ml/min. For the analysis, 100 μl of the sample are injected. The UV detection is carried out at 280 nm.

2.7: SDS-PAGE (Reduced/Nonreduced):

The quality of the samples in terms of the amount of covalent aggregates and of fragments was evaluated by analysis of the differences related to the weight of the proteins, by SDS-PAGE electrophoretic migration, under nonreducing conditions and under reducing conditions on a Novex system using gels in 2-(N-morpholino)ethanesulphonic acid or MES buffer (Invitrogen). An amount corresponding to 2 μg of protein was loaded. The proteins were visualized by Coomassie blue and/or silver nitrate staining.

2.8: IEF

The separation of the various FVII isoforms according to their isoelectric point was carried out by isoelectric focussing (IEF). The migration is carried out on a Focugel 3-10 ETC (Gelcompany) on a Multiphor system under native (nonreducing and nondenaturing) conditions. The product was subjected to desalting on a filtration unit (exclusion size 10 kDa). After having determined the concentration of the product via the OD at 280 nm, 30 μg were loaded onto the gel. The comparison of the populations contained in the product with the two different pI standards (standard pI 5.5-10.5 from GE and standard pI 5.4-5.9-6.6 from Sigma, loading of the individual standards) after staining with CBB-G250 (Coomassie Brilliant Blue G250) made it possible to identify the pI of the FVII isoforms (quantification using the Quantity one software, BioRad).

Results:

1. Formulations F1 to F8

In table 1 below, the formulations F1 and F2 are given by way of comparison.

Among the compositions according to the invention (F3 to F8), the formulations F3, F4 and F7 are preferred.

According to this table, the formulations F4, F5 and F7 show a percentage intensity of the monomeric population of the protein (respectively 58%, 61% and 55%) which is greater than those obtained in the NovoSeven® (F1) (9%) and NovoSeven RT® (F2) (27%) formulations. These results reflect an increase in the stability of the product in solid form and the presence of monomers makes it possible to decrease the risks of immunological reactions.

As regards the FVIIa/FVII:Ag ratio, the formulations F3, F4 and F8 exhibit FVIIa/FVII:Ag ratios before lyophilization and after reconstitution in liquid form that are higher than those obtained with formulations such as those of NovoSeven® (F1) and of NovoSeven RT® (F2), which reflects the fact that the protein (FVIIa) contained in the composition according to the invention is more active. An FVIIa/FVII:Ag ratio before lyophilization of 17 for F3 and 23 for F8 can be observed, compared with 14 for the ratios obtained with the NovoSeven® (F1) and NovoSeven RT® formulations, and an FVIIa/FVII:Ag ratio after reconstitution in liquid form of 19 for F3 and 20 for F8 can be observed, compared with 15 for the ratios obtained with the NovoSeven® (F1) and NovoSeven RT® formulations.

As regards the experiments carried out on the glass transition temperature (Tg), the formulations F3 to F8 according to the invention show an increase in the glass transition temperature. A glass transition temperature equal to 75° C. for the formulation F3, and of 93° C. for the formulation F7, are in particular obtained. These results show that the protein (FVIIa) is advantageously stable in these formulations. This is because a high Tg allows improved stability of the protein by reducing the mobility and the reactivity of the active ingredient. Furthermore, these results clearly show that the products according to the invention can be stored outside a refrigerator, contrary to the NovoSeven product from the company NovoNordisk.

As regards the filter test for aggregate detection, the results indicate that the formulations F3 to F8 according to the invention show few aggregates, or even a total absence of aggregates, for the formulations F4, F7 and F8.

As shown in FIG. 1, the activity of the FVII resulting from the formulation F3 (in liquid form after reconstitution) is still satisfactory after 6 days, with an activity of at least 80%.

Figure 2:
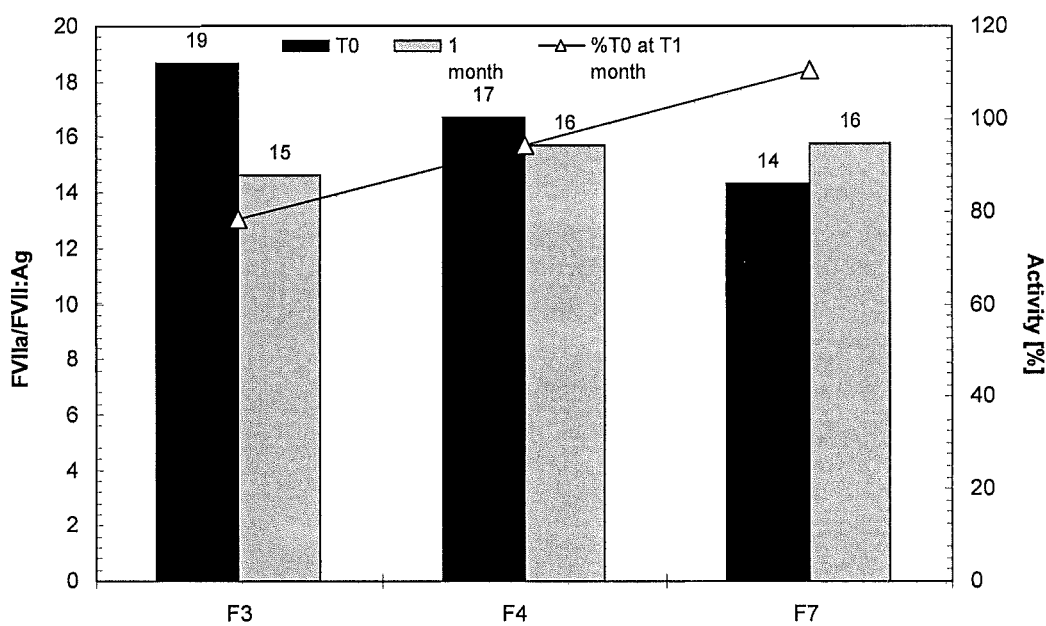
FIG. 2 is a graph which shows that the formulations F3, F4 and F7 in solid form make it possible to preserve the activity of the protein (FVIIa) (expressed by the FVIIa/FVII:Ag ratio) during storage at 40° C. for 1 month.

As shown in FIG. 2, the activity of the FVII resulting from the formulation F3 (in solid form) is still satisfactory after one month, with an activity of at least 80% for the formulation F3, and at least 90% for the formulation F4.

TABLE 1

Characteristics of the compositions prepared (F1 to F8) (comparative)

| Formulation identification | Buffer solution composition | FVIIa concentration | Visual aspect obtained according to the European Pharmacopoeia method Before lyophilization | Visual aspect obtained according to the European Pharmacopoeia method After reconstitution in liquid form | Size and % intensity after lyophilization of the monomeric population of the protein* Diameter (nm)* | Size and % intensity after lyophilization of the monomeric population of the protein* % intensity* | Ratio U/ml FVIIa/FVII:Ag Before lyophilization | Ratio U/ml FVIIa/FVII:Ag After reconstitution in liquid form | Tg (° C.) | Aggregate detection test |
|---|---|---|---|---|---|---|---|---|---|---|
| F1 Formulation similar to Novoseven | Glycylglycine (1.32 g/l) $CaCl_2 \cdot 2H_2O$ (1.47 g/l) NaCl (2.92 g/l) Mannitol (30 g/l) Polysorbate 80 (0.07 g/l) | 0.6 mg/ml | — | — | 7 | 9 | 14 | 15 | 45 | ++ |
| F2 Formulation similar to Novoseven RT | Methionine (0.5 g/l) Glycylglycine (1.32 g/l) $CaCl_2 \cdot 2H_2O$ (1.47 g/l) NaCl (2.92 g/l) Sucrose (10 g/l) Mannitol (25 g/l) Polysorbate 80 (0.07 g/l) | 0.6 mg/ml | — | — | 6 | 27 | 14 | 15 (Histidine) 15 (water) | 41 | ++ |
| F3 | Glycine (1.2 g/l) Lysine, HCl (1.2 g/l) Trisodium citrate•$2H_2O$ (1.5 g/l) Isoleucine (6 g/l) Arginine, HCl (24 g/l) | 0.6 mg/ml | — | — | 7 | 39 | 17 | 19 | 75 | + |
| F4 | Glycine (1.2 g/l) Lysine, HCl (1.2 g/l) Trisodium citrate•$2H_2O$ (1.5 g/l) Isoleucine (6 g/l) Arginine, HCl (24 g/l) Polysorbate 80 (0.07 g/l) | 0.6 mg/ml | — | — | 7 | 58 | 16 | 17 | 74 | ε |
| F5 | Glycine (1.2 g/l) Lysine, HCl (1.2 g/l) Trisodium citrate•$2H_2O$ (1.5 g/l) Arginine, HCl (30 g/l) Polysorbate 80 (0.07 g/l) | 0.6 mg/ml | — | — | 7 | 61 | 14 | 13 | 78 | ε |
| F6 | $CaCl_2 \cdot 2H_2O$ (0.15 g/l), Arginine, HCl (40 g/l) | 0.4 mg/ml | — | — | 7 | 21 | 13 | 13 | 84 | + |
| F7 | $CaCl_2 \cdot 2H_2O$ (0.15 g/l), Arginine, HCl (34 g/l), Isoleucine (6 g/l) | 0.4 mg/ml | — | — | 7 | 55 | 14 | 14 | 93 | ε |
| F8 | Trisodium citrate•$2H_2O$ (1 g/l), Arginine, HCl (30 g/l), Isoleucine (6 g/l) | 0.4 mg/ml | — | — | 7 | 23 | 23 | 20 | 91 | ε |

*size determined by DLS.
The compositions F1 and F2 are given by way of comparison and correspond to the NovoSeven ® (F1) and NovoSeven RT ® (F2) formulations.

2. Formulations F9 to F11—Stability Studies

The results of the tests carried out on these formulations are given in tables 2 to 4 below.

2.1 Stability Study: Formulation F9

The formulation F9 remains stable also after 6 months at 40° C., in lyophilized form. In addition, the results show that the FVII does not show any sign of obvious degradation after 6 months at 40° C.

2.2 Stability Study: Formulation F10

The studies carried out on the formulation F10 (Table 3) made it possible to show that the FVIIa is stable for 48 hours at 5° C., in liquid form.

As can also be seen in Table 2, the formulation F10 remains stable after four freezing/thawing cycles and the results obtained attest to an absence of degradation of the FVII.

The formulation F10 remains stable also after 6 months at 25° C. or at 40° C., in lyophilized form. The results of this study show that the FVII has not undergone any degradation.

The formulation F10 (non-lyophilized) remains stable also after 6 months frozen at a temperature below −70° C. The results obtained prove that the FVII has not undergone any degradation.

2.3 Stability Study: Formulation F11

The formulation F11 (Table 4) is stable after 6 months at 25° C. or at 40° C., in lyophilized form. The results of this study show that the FVII has not undergone any degradation.

The formulation F11 is stable also after 6 months frozen at a temperature below −70° C., in lyophilized form. The results obtained prove that the FVII has not undergone any degradation.

The study of stability of the formulation F11 in liquid form shows that the FVII remains stable during the 72 hours at 5° C. plus the 6 hours at 25° C.

TABLE 2

Characteristics of the compositions prepared (F9) (comparative)

| Formulation F9 | Visual appearance obtained according to the European Pharmacopoeia method | | % intensity of the population containing the protein in its monomeric form (measurement by DLS) | | Ratio U/ml FVIIa/FVII:Ag | | Aggregate detection test | MSD analyses (% monomers) | | SDS-PAGE and IEF |
|---|---|---|---|---|---|---|---|---|---|---|
| | T = 0 (after lyophilization) | T = 6 months | T = 0 (after lyophilization) | T = 6 months | T = 0 (after lyophilization) | T = 6 months | T = 6 months | T = 0 | T = 6 months | |
| Lyophilized at 40° C. | — | — | 61% | 52% | 16 | 16 | — | 86% | 90% | Comparable T = 0 and T = 6 months profiles |

TABLE 3

Characteristics of the compositions prepared (F10) (comparative)

| Formulation F10 | Visual appearance obtained according to the European Pharmacopoeia method | | % intensity of the population containing the protein in its monomeric form (measurement by DLS) | | Ratio U/ml FVIIa/FVII:Ag | | Aggregate detection test | MSD analyses (% monomers) | | SDS-PAGE and IEF |
|---|---|---|---|---|---|---|---|---|---|---|
| | T = 0 | T = 48 h at 5° C. | T = 0 | T = 48 h at 5° C. | T = 0 | T = 48 h at 5° C. | T = 48 h at 5° C. | T = 0 | T = 48 h at 5° C. | |
| Liquid at 5° C. | — | — | 73% | 70% | 16 | 14 | ε | 92% | 88% | Comparable T = 0 and T = 48 H 5° C. profiles |
| | T = 0 (after lyophilization) | T = 6 months | T = 0 (after lyophilization) | T = 6 months | T = 0 (after lyophilization) | T = 6 months | T = 6 months | T = 0 | T = 6 months | |
| Lyophilized at 25° C. | — | — | 55% | 71% | 16 | 16 | ε | 91% | 93% | Comparable T = 0 and T = 6 months profiles |
| Lyophilized at 40° C. | — | — | 55% | 65% | 16 | 15 | ε | 91% | 92% | Comparable T = 0 and T = 6 months profiles |

TABLE 3-continued

Characteristics of the compositions prepared (F10) (comparative)

| Formulation F10 | Visual appearance obtained according to the European Pharmacopoeia method | | % intensity of the population containing the protein in its monomeric form (measurement by DLS) | | Ratio U/ml FVIIa/FVII:Ag | | Aggregate detection test | | MSD analyses (% monomers) | | SDS-PAGE and IEF |
|---|---|---|---|---|---|---|---|---|---|---|---|
| Freezing at <−70° C. | — | — | 73% | 87% | 16 | 16 | ϵ | | 92% | 92% | Comparable T = 0 T = 6 months profiles |
| | T = 0 | T = 4 cycles | T = 0 | T = 4 cycles | T = 0 | T = 4 cycles | T = 0 | T = 4 cycles | T = 0 | T = 4 cycles | |
| 4 freezing/ thawing cycles | — | — | 73% | 63% | 16 | 13 | ϵ | | 92% | 89% | Comparable T = 0 and T = 4 cycles profiles |

TABLE 4

Characteristics of the compositions prepared (F11) (comparative)

| Formulation F11 | Visual appearance obtained according to the European Pharmacopoeia method | | % intensity of the population containing the protein in its monomeric form (measurement by DLS) | | Ratio U/ml FVIIa/FVII:Ag | | Aggregate detection test | MSD analyses (% monomers) | | SDS-PAGE and IEF |
|---|---|---|---|---|---|---|---|---|---|---|
| | T = 0 | T = 72 h at 5° C. + 6 h at 25° C. | T = 0 | T = 72 h at 5° C. + 6 h at 25° C. | T = 0 | T = 72 h at 5° C. + 6 h at 25° C. | T = 72 h at 5° C. + 6 h at 25° C. | T = 0 | T = 72 h at 5° C. + 6 h at 25° C. | |
| Liquid at 5 °C. | — | — | 65% | 66% | 15 | 21 | NP | NP | NP | NP |
| | T = 0 (after lyoph- ilization) | T = 6 months | T = 0 (after lyoph- ilization) | T = 6 months | T = 0 (after lyoph- ilization) | T = 6 months | T = 6 months | T = 0 | T = 6 months | |
| Lyophilized at 25° C. | — | — | 65% | 66% | 19 | 20 | ϵ | 98% | 93% | Comparable T = 0 and T = 6 months profiles |
| Lyophilized at 40° C. | — | — | 65% | 55% | 19 | 19 | ϵ | 98% | 97% | Comparable T = 0 and T = 6 months profiles |
| Freezing at <−70° C. | — | — | 87% | 87% | 19 | 18 | ϵ | NP | 97% | Comparable T = 0 and T = 6 months profiles |

NP = not performed

The invention claimed is:

1. A pharmaceutical composition in liquid form or in solid form, comprising factor VII, said composition being free of mannitol, of sucrose, or of glycyiglycine, said composition further comprising i) at least one hydrophilic amino acid or amino acid bearing a positively charged side chain, and ii) at least one amino acid having an apolar side-chain.

2. The pharmaceutical composition of claim 1 in liquid form.

3. The pharmaceutical composition of claim 1 in lyophilized form.

4. The pharmaceutical composition of claim 1, said composition being free of any sugar, of polyol, or of methionine.

5. The pharmaceutical composition of claim 2, said composition being free of any sugar, of polyol, or of methionine.

6. The pharmaceutical composition of claim 3, said composition being free of any sugar, of polyol, or of methionine.

7. The pharmaceutical composition of claim 1, in which the factor VII is in activated form (FVIIa).

8. The composition of claim 1, wherein Factor VII is obtained by genetic engineering from cells or from transgenic animals.

9. The pharmaceutical composition of claim 1, further comprising an alkali metal salt, an alkaline-earth metal salt, or a transition metal salt.

10. The pharmaceutical composition of claim 1, comprising:
factor VII,
arginine, isoleucine,
lysine,
glycine,
trisodium citrate or calcium chloride, and
polysorbate 80 or polysorbate 20.

11. The pharmaceutical composition of claim 10, comprising:
factor VII,
from 10 to 40 g/l of arginine,
from 4.2 to 6.6 g/l of isoleucine,
from 0.6 to 1.8 g/l of lysine,
from 0.6 to 1.8 g/l of glycine,
from 1 to 2 g/l of trisodium citrate dihydrate or from 0 to 0.2 g/L of calcium chloride dihydrate, and
from 0 to 0.5 g/l of polysorbate 80.

12. The pharmaceutical composition of claim 11, comprising:
factor VII at 0.2 to 2 g/l,
arginine hydrochloride at 24 g/l,
isoleucine at 6 g/l,
trisodium citrate dihydrate at 1.5 g/l,
glycine at 1.2 g/l,
lysine hydrochloride at 1.2 g/l, and, optionally,
polysorbate 80 at 0.07 g/l.

13. The pharmaceutical composition of claim 10, comprising:
factor VII at 0.2 to 2 g/l,
arginine hydrochloride at 34 g/l,
calcium chloride dihydrate at 0.15 g/l, and
isoleucine at 6 g/l.

14. A lyophilized solid composition which can be obtained from the composition of claim 1.

15. An injectable formulation obtained by means of a method comprising dissolving a solid composition as defined in claim 1, in water.

16. A method for preparing a pharmaceutical composition according to claim 1, said method comprising mixing the FVII with a buffer solution, adjusting the pH if necessary, filtering, and then desiccating if necessary so as to obtain the solid form.

17. A method for preparing an injectable formulation for therapeutic use, said method comprising dissolving a solid composition as defined in claim 1, in water for injection.

18. A method for treating haemophilia or congenital factor VII deficiency, the method comprising administering a pharmaceutical composition as defined in claim 1 to a patient in need thereof.

19. A method for treating haemophilia or congenital factor VII deficiency, the method comprising administering an injectable formulation as defined in claim 15 to a patient in need thereof.

* * * * *

UNITED STATES PATENT AND TRADEMARK OFFICE
CERTIFICATE OF CORRECTION

PATENT NO. : 9,358,275 B2  
APPLICATION NO. : 14/687499  
DATED : June 7, 2016  
INVENTOR(S) : Annie Bardat et al.

Page 1 of 1

It is certified that error appears in the above-identified patent and that said Letters Patent is hereby corrected as shown below:

In the claims,

Column 17, line 56, in claim 1, line 3, change "glycyiglycine" to --glycylglycine--.

Signed and Sealed this
Sixteenth Day of August, 2016

Michelle K. Lee
*Director of the United States Patent and Trademark Office*